US00PP37470P2

(12) United States Plant Patent
van Swieten

(10) Patent No.: US PP37,470 P2
(45) Date of Patent: Jun. 16, 2026

(54) ***PHALAENOPSIS* PLANT NAMED 'PHA925456'**

(50) Latin Name: *Phalaenopsis hybrida*
Varietal Denomination: PHA925456

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/316,700

(22) Filed: Sep. 2, 2025

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

U.S. PATENT DOCUMENTS

PP32,282 P2 * 10/2020 Van Swieten ..... A01H 5/02
Plt./311

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'PHA925456', characterized by its upright plant habit; moderately vigorous growth habit and moderate growth rate; strong flowering stems; freely flowering habit with typically two inflorescences developing per plant, each inflorescence with numerous flowers; medium to broad flowers with white-colored petals and sepals with dark purplish red-colored blotches and spots; and good postproduction longevity.

2 Drawing Sheets

Figure 1:
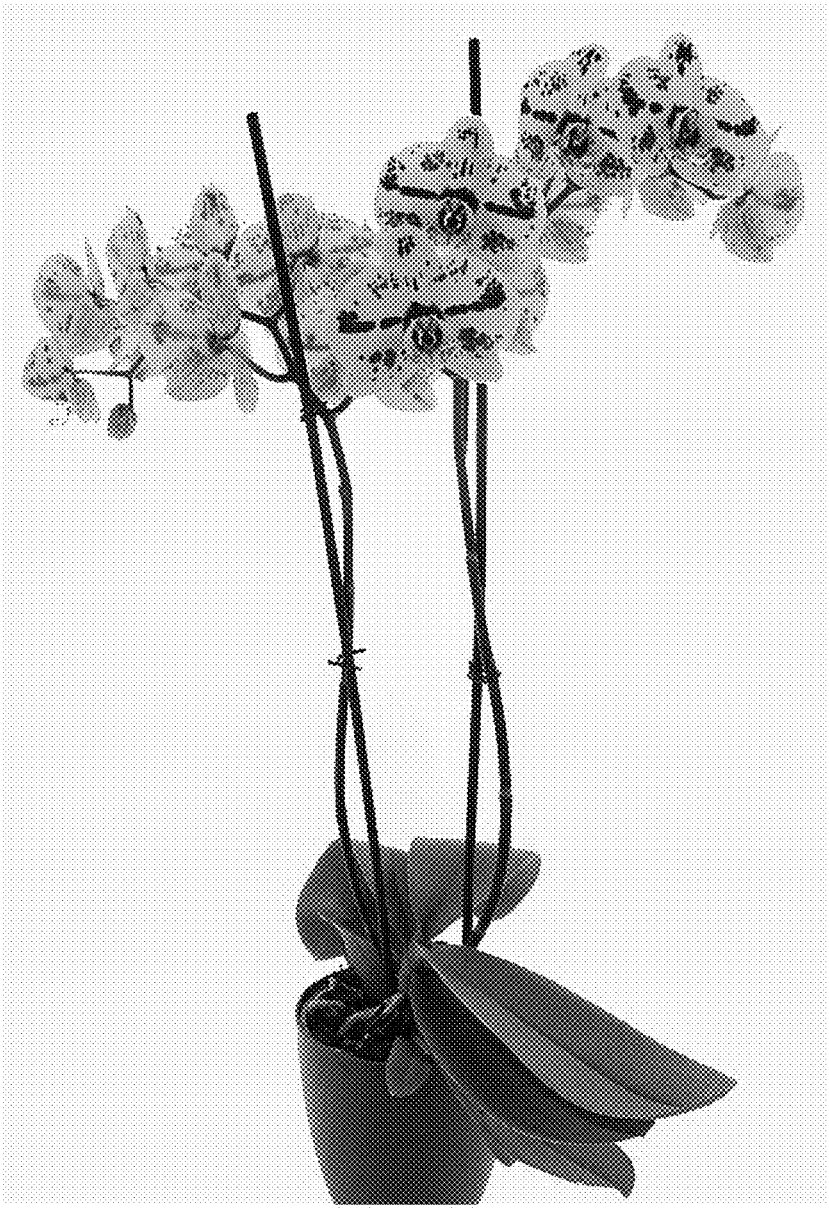

Botanical designation: *Phalaenopsis hybrida.*
Cultivar denomination: 'PHA925456'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Aug. 14, 2024, application number 2024/1903. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA925456'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique patterns and coloration.

The new *Phalaenopsis* plant originated from a cross-pollination in January, 2017 in Bleiswijk, The Netherlands of a proprietary breeding selection of *Phalaenopsis hybrida* identified as code number 13-057464-0002, not patented, as the female, or seed, parent with a proprietary breeding selection of *Phalaenopsis hybrida* identified as code number 13-057783-0001, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in October, 2019.

Asexual reproduction of the new *Phalaenopsis* plant by in vitro meristem propagation in a controlled environment in Bleiswijk, The Netherlands since October, 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA925456'. These characteristics in combination distinguish 'PHA925456' as a new and distinct *Phalaenopsis* plant:

1. Upright plant habit.
2. Moderately vigorous growth habit and moderate growth rate.
3. Strong flowering stems.
4. Freely flowering habit with typically two inflorescences developing per plant, each inflorescence with numerous flowers.

5. Medium to broad flowers with white-colored petals and sepals with dark purplish red-colored blotches and spots.
6. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are horizontal to semi-drooping in aspect whereas leaves of plants of the female parent selection are semi-erect in aspect.
2. The leaf apices of plants of the new *Phalaenopsis* are moderately asymmetric whereas the leaf apices of plants of the female parent selection are symmetric or slightly asymmetric.
3. The dorsal sepal apices of plants of the new *Phalaenopsis* are obtuse and shallow retuse whereas the dorsal sepal apices of the female parent selection are obtuse and not emarginate.

Plants of the new *Phalaenopsis* can be compared to plants of the male parent selection. Plants of the new *Phalaenopsis* differ primarily from plants of the male parent selection in labella shape as the lateral lobes of the labella of plants of the new *Phalaenopsis* are more inwardly curved than the lateral lobes of the labella of plants of the male parent selection.

Plants of the new *Phalaenopsis* can be compared to plants of *Phalaenopsis hybrida* 'PHALGYTCAN', disclosed in U.S. Plant Pat. No. 32,282. In side-by-side comparisons, plants of the new *Phalaenopsis* differ primarily from plants of 'PHALGYTCAN' in petal and sepal color as petals and sepals of plants of the new *Phalaenopsis* have smaller blotches and spots than petals and sepals of plants of 'PHALGYTCAN'. In addition, leaves of plants of the new *Phalaenopsis* are shorter than leaves of plants of 'PHALGYTCAN'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA925456' grown in a container.

Figure 2:
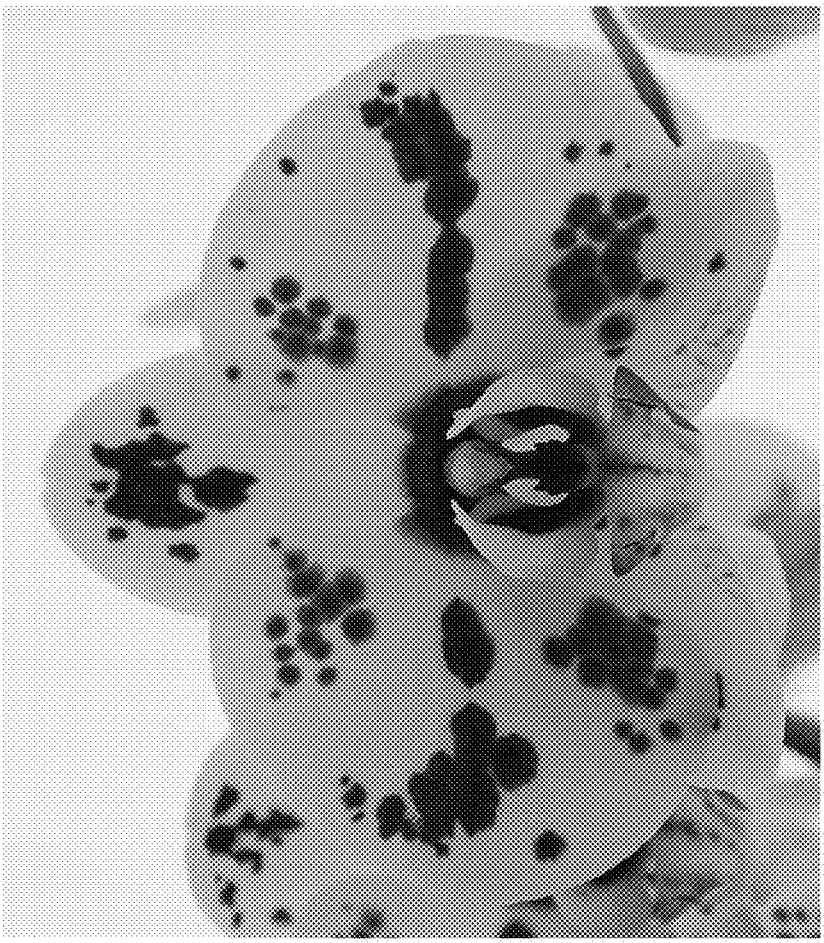

The photograph on the second sheet (FIG. 2) is a close-up view of a typical flower of 'PHA925456'.

DETAILED BOTANICAL DESCRIPTION

The aforementioned photographs and following observations and measurements describe plants grown during the winter in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA925456'.

Parentage:

*Female, or seed, parent*.—Proprietary breeding selection of *Phalaenopsis hybrida* identified as code number 13-057464-0002, not patented.

*Male, or pollen, parent*.—Proprietary breeding selection of *Phalaenopsis hybrida* identified as code number 13-057783-0001, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane*.—About 12.8 cm.

*Plant height, substrate level to top of floral plane*.—About 52.7 cm.

*Plant diameter or spread*.—About 41.1 cm.

Leaf description:

*Arrangement and quantity*.—Distichous, simple; sessile; about four to seven fully-developed leaves per plant.

*Length*.—About 22.7 cm.

*Width*.—About 7 cm.

*Aspect*.—Horizontal to semi-drooping.

*Shape*.—Oblanceolate; slightly carinate.

*Apex*.—Unequal obtuse.

*Base*.—Sheathing. Sheath length: About 2.2 cm. Sheath width: About 1.5 cm. Sheath color: Close to 144A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to a blend of 137A and 146A; narrow marginal edges, close to 137C. Developing leaves, lower surface: Close to 146A; narrow marginal edges, close to NN137B. Fully expanded leaves, upper surface: Close to NN137B; narrow marginal edges, close to 137C; venation, close to NN137A. Fully expanded leaves, lower surface: Close to 146B; narrow marginal edges, close to blend of 146A and 147A; venation, close to 137A.

Inflorescence description:

*Appearance and flowering habit*.—Showy zygomorphic flowers arranged on axillary simple or branched racemes; typically two inflorescences develop per plant; each inflorescence with about ten to eleven flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about eleven weeks on the plant; flowers not persistent.

*Inflorescence length* (*lowermost flower to inflorescence apex*).—About 26.6 cm.

*Inflorescence width*.—About 16.8 cm.

*Flower buds*.—Height: About 1.9 cm. Diameter: About 1.4 cm by 1.6 cm. Shape: Broadly ovate. Color: Close to 145B; upper surface and venation, close to 177B and 177C.

*Flower size*.—About 7.7 cm (vertical) by 9.2 cm (horizontal).

*Flower depth*.—About 2.8 cm.

*Petals, quantity and arrangement*.—Three, two lateral petals and one center petal transformed into a labellum.

*Lateral petals*.—Length: About 4.3 cm. Width: About 5.5 cm. Shape: Broadly reniform. Apex: Obtuse and shallow retuse. Margin: Entire; not undulate. Texture and luster, upper and lower surfaces: Smooth, glabrous; moderately velvety; matte. Color: When opening, upper surface: Close to NN155D; blotches and spots loosely following the midvein, close to 187B and 187C; random blotches and spots, close to N79A, N79B and N79C; at the base, close to N79A and N79B. When opening, lower surface: Close to NN155D; blotches and spots loosely following the midvein, close to N77A; random blotches and spots, close to N77B; at the base, close to 187B. Fully opened, upper surface: Close to NN155D; blotches and spots loosely following the midvein, close to N186D; random blotches and spots, close to N79A, N79C and N79D; at the base, close to N79A to N79C; colors do not change with subsequent development. Fully opened, lower surface: Close to NN155D; blotches and spots loosely following the midvein, close to N77B and N77C; random blotches and spots, close to 75B, 76B and N77B; at the base, close to N77B; colors do not change with subsequent development.

*Labella*.—Appearance: Three-parted with two lateral lobes and a central lobe; overall shape, broadly cordate. Length, lateral lobes: About 2.2 cm. Width, lateral lobes: About 1.7 cm. Length, central lobe: About 2.2 cm. Width, central lobe: About 8 mm to 24 mm. Length, cirrhose tips: About 1 cm. Shape, lateral lobes: Obovate. Shape, central lobe: Kite-shaped with a slightly elongated apex. Apex, lateral lobes: Obtuse. Apex, central lobe: Acute with cirrhose apices facing upwards and backwards. Margins, lateral and central lobes: Entire. Texture and luster, lateral and central lobes, upper and lower surfaces: Smooth, glabrous; velvety; matte. Callosities: Located at the base of the labellum and attachment point of the lateral petals; about 4 mm in length, about 6 mm in width and about 6 mm in height. Color: When opening, upper surface: Lateral lobes: Close to NN155D; lower 25%, close to 5A; occasionally with a few small dots, close to 77B; at the base, close to 187A. Central lobe: Close to NN155D; towards the base, close to 12B; at the margins, close to N78B and N78C; fine dots, close to 166C; at the base, close to 200B and 76A; midvein, close to N77A and N77B; cirrhose apices, close to N186C with margins and base, close to NN155D. Callosities: Close to 16B; towards the margins and base, close to 200B. When opening, lower surface: Lateral lobes: Close to NN155D; lower 25%, close to 6A; occasionally with a few small dots, close to 77D; at the base, close to N187C and N187D. Central lobe: Close to NN155D; towards the base, close to 160A and 160B; at the margins, close to 77B and 77C; fine dots, close to 166C and 166D; at the base, close to a blend of N77D and 201D; midvein, close to N77B; cirrhose apices, close to N186C with margins and base, close to NN155D. Fully opened, upper surface: Lateral lobes: Close to NN155D; lower 25%, close to 5A; occasionally with a few small dots, close to 77B; at the base, close to 187A. Central lobe: Close to NN155D; towards the base, close to 12B; at the margins, close to N78C; fine dots, close to 166C and 166D; at the base, close to 200B and 76A; midvein, close to N77A and N77B; cirrhose apices, close to N186C with margins and base, close to NN155D. Callosities: Close to 13C; towards the apex, close to 200B. Fully opened, lower surface: Lateral lobes: Close to NN155D; lower 25%, close to 7B; occasionally with a few small dots, close to 77D; at the base, close to N187C and N187D. Central lobe: Close to NN155D; towards the base, close to 160A and 160B; at the margins, close to 77C; fine dots, close to 166D; at the base, close to a blend of N77D and 201D; midvein, close to N77C; cirrhose apices, close to N186C with margins and base, close to NN155D.

*Sepals*.—Quantity and arrangement: Three, one upper dorsal sepal and two lower lateral sepals. Length, dorsal sepal: About 4.4 cm. Width, dorsal sepal: About 3 cm. Length, lateral sepals: About 4.5 cm. Width, lateral sepals: About 3 cm. Shape, dorsal sepal: Elliptic-oblong. Shape, lateral sepals: Ovate. Apex, dorsal sepal: Obtuse to shallow retuse, emarginate. Apex, lateral sepals: Bluntly acute. Base, dorsal and lateral sepals: Cuneate. Margins, dorsal and lateral sepals: Entire; not undulate. Texture and luster, dorsal and lateral sepals, upper surface: Smooth, glabrous; velvety; matte. Texture and luster, dorsal and lateral sepals, lower surface: Smooth, glabrous; moderately velvety; matte. Color, dorsal sepal: When opening, upper surface: Close to NN155C; blotches and spots along the margins and loosely following the veins, close to 187A and 187B; at the base, close to N79A and N79B; occasional fine venation, close to N80B. When opening, lower surface: Close to 76B; broad apical margins, close to 155C; irregular blotches and spots, close to N77A and N77C; towards the base, close to 196C and at the base, close to N79B. Fully opened, upper surface: Close to NN155D; blotches and spots along the margins and loosely following the veins, close to a blend of N79A and 187A and a blend of N79B and 187B; at the base, close to N79A and N79B. Fully opened, lower surface: Close to 76B and 76C; broad apical margins, close to NN155D; irregular blotches and spots, close to N77B and N77C; at the base, close to N79B. Color, lateral sepals: When opening, upper surface: Close to NN155C; lower half, close to a blend of 145D and 157C; blotches and spots along the margins and loosely following the veins, close to 187B and 187C; at the base, close to N79A; occasional fine venation, close to N80B. When opening, lower surface: Close to a blend of 145C and 145D; towards the apex, tinged with close to N77B; irregular blotches and spots, close to N77A and N77C; at the base, close to N79B; midvein, close to 70A. Fully opened, upper surface: Close to NN155C; blotches and spots along the margins and loosely following the veins, close to N79B and N79C; towards the base, close to 155C and at the base, close to N79B and N79C. Fully opened, lower surface: Close to 76A and 76B; center, tinged with close to 157B; apical margins, close to 155C; irregular blotches and spots, close to N77C and N77D; at the base, close to N79B; midvein, close to 77C.

*Peduncles*.—Length: About 56 cm. Diameter: About 6 mm. Strength: Strong. Aspect: Upright to outwardly arching. Texture and luster: Smooth, glabrous; matte. Color: Close to 200A with dense fine dots, close to 147B.

*Pedicels*.—Length: About 4 cm. Diameter: About 3 mm. Strength: Moderately strong. Aspect: About 70° from peduncle axis. Texture and luster: Smooth, glabrous; matte. Color: Close to 145A; proximally, close to N77B and at the base, close to a blend of N186C and 200A; distally, close to 75C.

*Reproductive organs*.—Androecium: Column length: About 8 mm. Column width: About 6 mm. Column color: Close to N78A; towards the apex, close to NN155C. Pollinia quantity: Two. Pollinia diameter (per two pollinia): About 2.5 mm. Pollinia color: Close to 23A. Gynoecium: Stigma length: About 2.5 mm. Stigma width: About 4.5 mm. Stigma shape: Reniform. Stigma color: Close to 76B with margins, close to N79C. Ovary length: About 1.1 cm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA925456' as herein illustrated and described.

* * * * *